United States Patent
Gorton (10) Patent No.: US 10,414,658 B2
(45) Date of Patent: Sep. 17, 2019

(54) GRAPHENE COATED PARTICLES, THEIR METHOD OF MANUFACTURE, AND USE

(71) Applicants: Millman Systems LLC, Harwood, MD (US); Stephen Jeffery Gorton, Rowlett, TX (US)

(72) Inventor: Stephen Jeffery Gorton, Rowlett, TX (US)

(73) Assignee: Millman Systems LLC, Harwood, MD (US)

( * ) Notice: Subject to any disclaimer, the term of this patent is extended or adjusted under 35 U.S.C. 154(b) by 0 days.

(21) Appl. No.: 15/932,667

(22) PCT Filed: Feb. 15, 2017

(86) PCT No.: PCT/US2017/000014
§ 371 (c)(1),
(2) Date: Apr. 6, 2018

(87) PCT Pub. No.: WO2017/142632
PCT Pub. Date: Aug. 24, 2017

(65) Prior Publication Data
US 2018/0215624 A1     Aug. 2, 2018

Related U.S. Application Data

(60) Provisional application No. 62/296,537, filed on Feb. 17, 2016.

(51) Int. Cl.
| | | |
|---|---|---|
| *B82Y 5/00* | (2011.01) | |
| *B82Y 40/00* | (2011.01) | |
| *B82Y 30/00* | (2011.01) | |
| *C01B 32/194* | (2017.01) | |
| *C01B 32/184* | (2017.01) | |
| *C01B 32/19* | (2017.01) | |

(52) U.S. Cl.
CPC .......... *C01B 32/194* (2017.08); *C01B 32/184* (2017.08); *C01B 32/19* (2017.08); *B82Y 5/00* (2013.01); *B82Y 30/00* (2013.01); *B82Y 40/00* (2013.01); *Y10S 977/734* (2013.01); *Y10S 977/847* (2013.01)

(58) Field of Classification Search
CPC ............ B82Y 30/00; B82Y 40/00; B82Y 5/00
See application file for complete search history.

(56) References Cited

U.S. PATENT DOCUMENTS

| | | | | |
|---|---|---|---|---|
| 2012/0102843 | A1* | 5/2012 | Chakraborty | C01B 32/28 51/295 |
| 2013/0224594 | A1* | 8/2013 | Yushin | H01M 4/38 429/218.1 |
| 2014/0011034 | A1* | 1/2014 | Majumder | C02F 1/288 428/406 |
| 2015/0263342 | A1* | 9/2015 | Newbound | H01M 10/0565 427/122 |

* cited by examiner

*Primary Examiner* — Audrea B Coniglio (57) ABSTRACT

Disclosed is a composition of matter comprising a biologically active substance bound to a graphene-coated dielectric-core particle, and methods for making and using the same.

7 Claims, 7 Drawing Sheets

GRAPHENE COATED PARTICLES, THEIR METHOD OF MANUFACTURE, AND USE

REFERENCE TO RELATED APPLICATIONS

This application claims priority to U.S. provisional application 62/296,537, filed 17 Feb. 2016, the contents of which are incorporated herein in their entirety.

TECHNICAL FIELD

The following inventive concepts relate to particles coated with graphene having chemical groups attached, their manufacture, and use.

BACKGROUND ART

Graphene is a form of carbon characterized by a flat hexagonal aromatic lattice of carbon atoms. Graphene, applied to a substrate in a single layer or sheet, is seeing increasing scientific use a basic material in industrial production and scientific research, due to its interesting electrical and physical properties. However, there are limits to its current use. Primarily, it is difficult to both apply chemical and electrical functionalities to bulk graphene and have that "activated" graphene attached to a usable substrate for distribution. Therefore, a need exists to provide mechanisms to create and distribute such particles.

Further, delivering biologically active substances to targets is an ever-present problem in the pharmaceutical, herbicide, pesticide, fertilizers, fungicide, and water treatment industries, amongst others. Therefore, a solution to this problem is also sought.

DISCLOSURE OF INVENTION

Embodiments of the present invention may provide for a graphene coated, chemically active particle comprising a silica core, a graphene layer surrounding the core, and negatively charged moieties or basic moieties attached to the outer surface of the graphene layer.

Embodiments may also provide for a method for creating a biologically active graphene based substrate as provided above, additionally comprising binding a biologically active peptide to a metal ion, the method comprising adding graphite to a solution of weak base, neutralizing the solution with a weak acid substance, super-heating the solution, then immersing a metal in an electrolyte solution with a dissimilar metal, neutralizing the electrolyte solution, adding a polypeptide to the metal electrolyte solution, and combining the peptide/electrolyte solution with the graphene solution.

Embodiments may also provide for a method to bind biologically active molecules and organisms in-situ to graphene coated charged particles, comprising spraying or soaking the chemically active graphite particle solutions described above over in-situ biological molecules or organisms.

Embodiments of the present invention can provide for a method of manufacturing a charged, graphene coated particle comprising: adding graphite to a weak basic solution, neutralizing the solution with a weak acid substance, immersing a metal in an electrolyte solution with a dissimilar metal, combining the graphite and metal solutions, adding a silica substrate to the mixed solution, and super-heating the mixed solution.

BRIEF DESCRIPTION OF THE DRAWINGS

The figures herein are schematic, and are not necessarily to scale. Features may be exaggerated for simplicity or to assist understanding. Skilled practitioners will recognize that some components or steps may have been omitted for simplicity, and that other components or steps may be added without deviating from the underlying concepts disclosed herein.

BEST MODE FOR CARRYING OUT THE INVENTION

The inventive concepts disclosed herein are described with respect to particular example embodiments and processes along with some explanations for their operation, however, one skilled in the art will recognize that the underlying principles disclosed may be embodied in other examples or methods not necessarily identical to the given examples. Therefore, the limits of the inventive concepts are to be taken as the claimed subject matter, and not the individual examples themselves.

Figure 1:
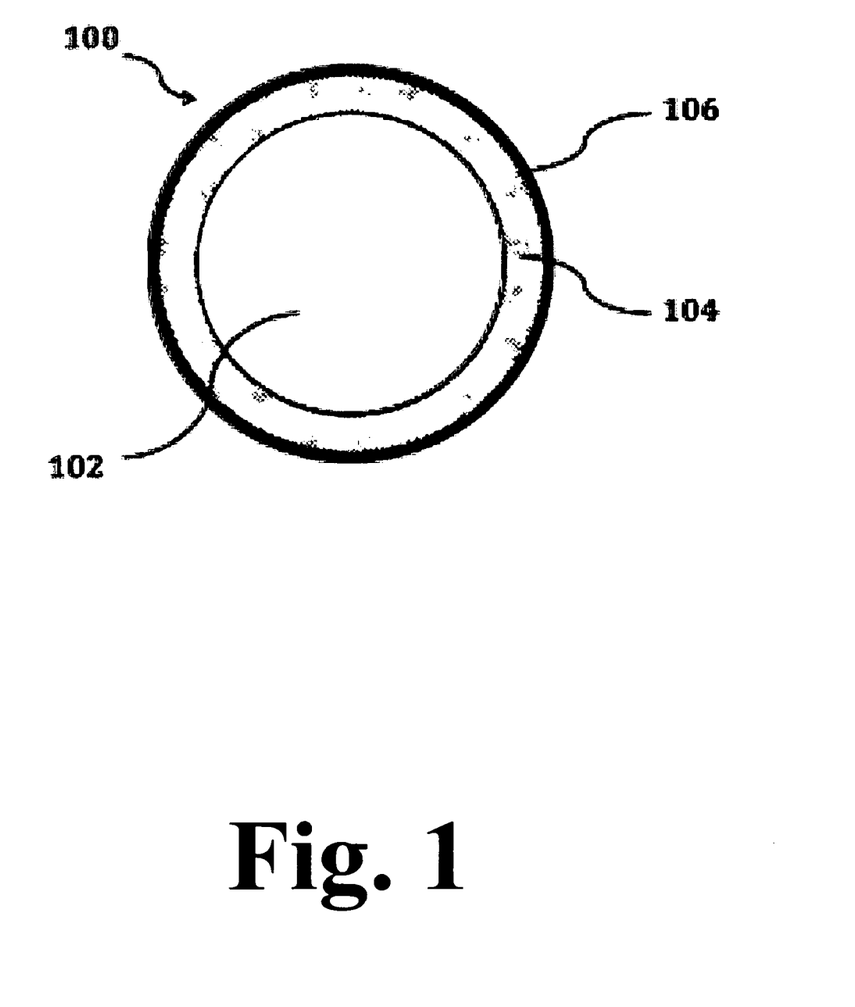
FIG. 1 is a schematic, cross-sectional view of an example of chemically active graphene/core particle complex, according to some inventive aspects.

Shown in FIG. 1 is a simplified cross-sectional view of an example of a chemically active graphene coated particle 100 (sometimes referred to briefly as a graphene coated particle 100) according to aspects of the inventive concepts. The example complex can be described as a core particle 102 that is coated with a graphene shell 104 having chemically active groups 106 attached to the graphene. In some embodiment, the chemically active groups 106 may be negatively charged or basic groups on the graphene shell's outer surface.

The core material used herein is an inert material that exhibits dielectric properties. More particularly, in some embodiments, the core particle 102 may be a silica (or mostly silica) structure such as finely divided and screened silica, diatomaceous earth, coal, or other similar largely inert material. The chemically active group 106, such as the e.g. negatively charged or basic group may be evenly or unevenly distributed over the graphene shell 104 (depicted here as a layer due to the relatively small nature of the groups). The physical structure of the core material may be non-uniform and may contain multiple flat surfaces where the surfaces are multi angled, and/or multi-dimensional. In some embodiments, the negatively charged or basic group (chemically active group 106) may be a hydroxy group. The construction of graphene particle 100 will be discussed below with regard to FIG. 6.

Figure 2:
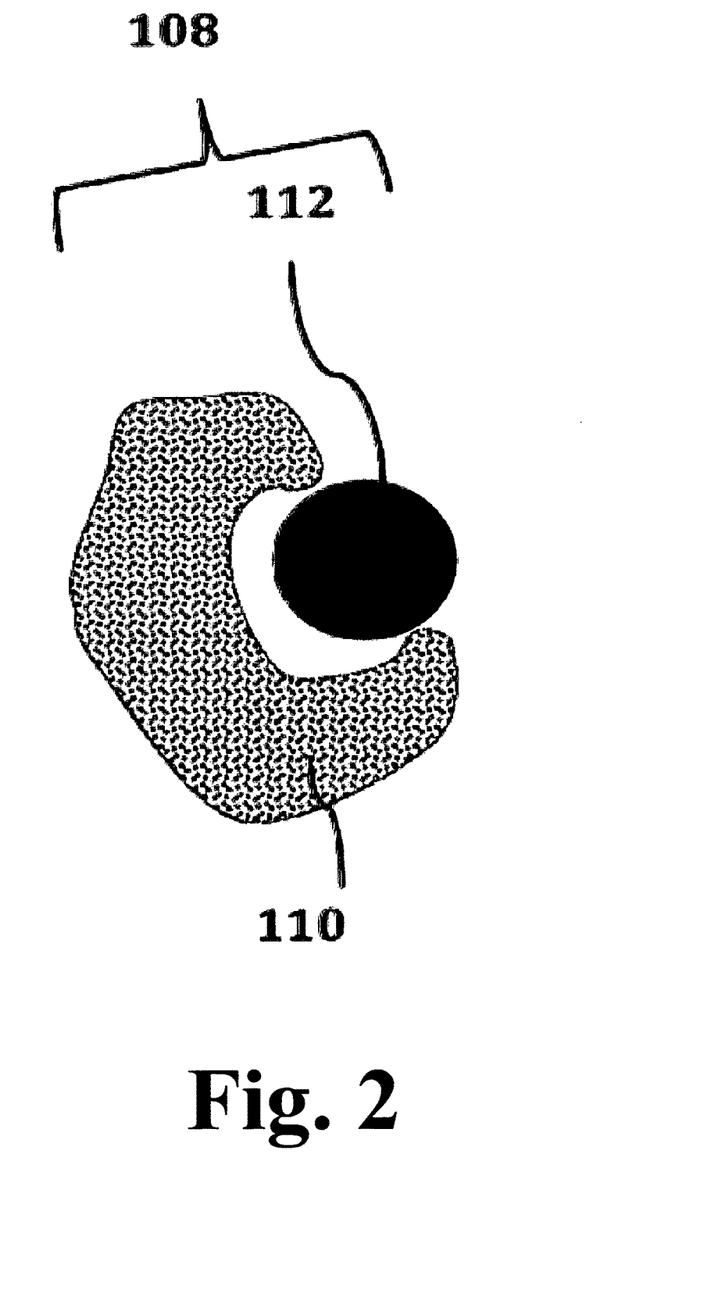
FIG. 2 is a schematic, simplified cross-sectional view of an example of a metal-attached polypeptide, according to some inventive aspects.

Shown in FIG. 2 is a simplified cross-sectional view of an example of a metal-attached polypeptide 108, according to aspects of the inventive concepts, which may be comprised of a polypeptide or protein 110, and metal ion 112 bound to its active site, in some instances imparting an overall positive charge (or regional or "local" positive charge) to the polypeptide 108. In some embodiments, multiple metal ions may be bound by a polypeptide, or multiple polypeptides may bind a single metal ion in concert. The polypeptide 110 may be a stand-alone polypeptide or protein, or one attached to an organism (such as being part of an organism's cell wall or outer membrane), which is depicted in FIG. 3.

Figure 3:
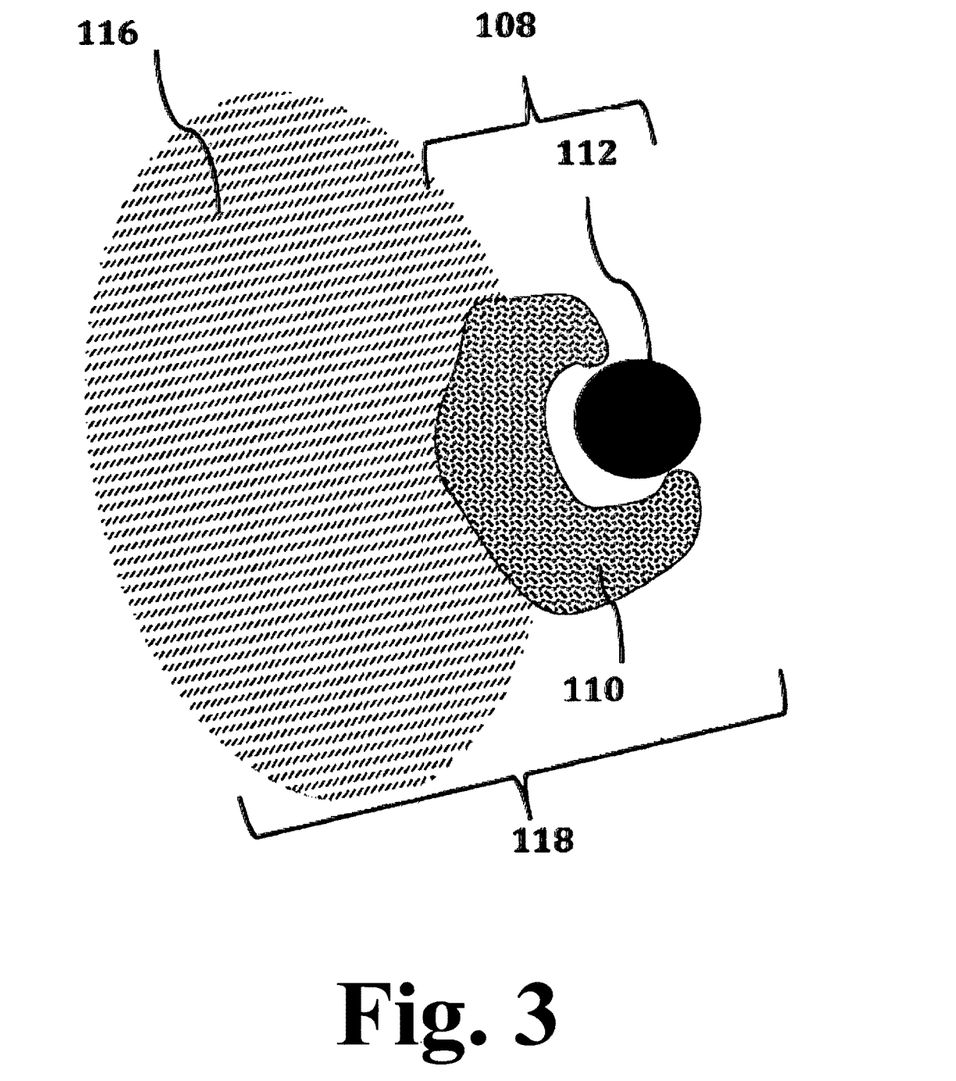
FIG. 3 is a schematic, simplified cross-sectional view of an example of a metal-attached single cell organism, according to some inventive aspects.

Shown in FIG. 3 is a simplified cross-sectional view of an example of a single cell organism 116 having at least one protein 110 holding a metal ion 112 (i.e., a metal-attached polypeptide 108), the complex of which is referred to as a biologically active organism/"charged cell" complex 118 (although the charge may be local only). The metal-attached polypeptide 108 may be located approximately on the outer surface of a single celled organism 116, such as in the outer membrane or cell wall. The single celled organism 116 may be an organism such as a prokaryote or eukaryote, and these may have a one or more metal-attached polypeptides 108, on their surface at multiple locations. Alternatively, the charged cell 118 shown in FIG. 3 may be part of a multi-cell organism, with the other cells not shown for clarity. For the sake of clarity, 118 will be referred to as "charged cell" 118. The delivery of metal ions to the polypeptide, and its relationship to the graphene particle 100 will be discussed below.

Figure 4:
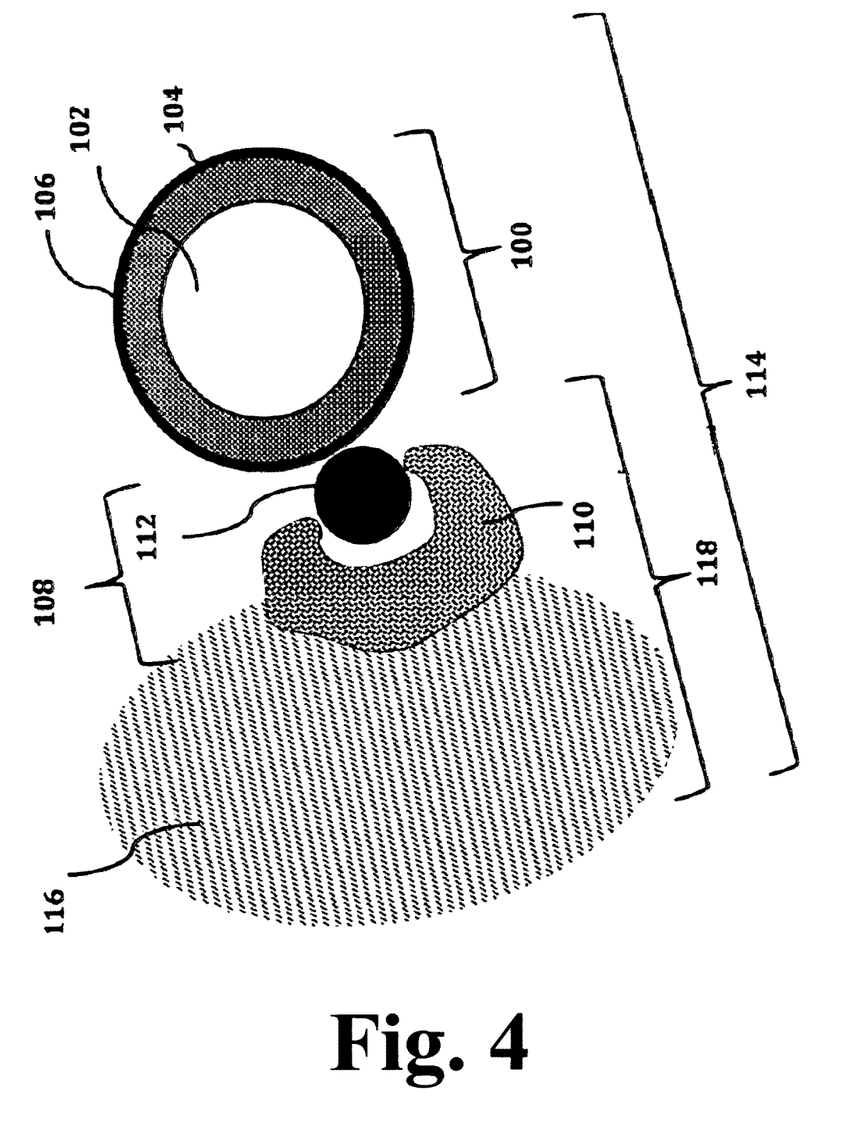
FIG. 4 is a schematic, simplified cross-sectional view of an example of a chemically active graphene coated particle complexed with a metal-bound single celled organism, according to some embodiments of the invention.

Shown in FIG. 4 is a simplified cross-sectional view of an example of a graphene particle 100 bound to a cell 116 having at least one metal-attached polypeptide 108 (hereinafter "complex 114"), according to aspects of the inventive concepts. More specifically, the complex 114 can comprise a graphene-coated core particle 100 as depicted and described in FIG. 1, chemically bound (through ionic, covalent, or other chemical binding means) to the metal of the metal-attached polypeptide 108 (depicted and described in FIG. 2), which in turn may be stand-alone or located on a cell 110, the state of which is depicted and described in FIG. 3 as the charged cell 118.

In some embodiments, the complex 114 can be produced by combining the metal-attached polypeptide 108, or charged cell 118, together with the chemically active graphene complex 100, each of which holds respective ionic charges: 112 (a positive charge or metal ion, such as one or more of the transition metals of manganese, iron, copper, zinc, etc.) and 106 (a negative charge or base, such as a sodium, potassium, or ammonium base salts) that are attracted towards one another.

More specifically, in some embodiments, the positively charged metal ion 112—which gives the polypeptide 110 located on charged cell containing organism 116 (or overall, the charged cell 118 possessing polypeptide 110) its charge—binds at the active site[s] ("receptors") of the polypeptide 110. Meanwhile, the negatively charged/basic surface coating 106 on the charged graphene complex 100 is a chemical component attached to graphene shell 104 of graphene particle 100. These two components attract each other to form overall complex 114.

In some embodiments, there may be a multiplicity of metal-bound polypeptides 108 or charged cells 118 complexed with each graphene coated particle 100. In other embodiments, each charged cell 118 may have multiple graphene coated particles 100 complexed with it. The distribution of the chemically graphene complexes 100 over the surface of a charged cell 118 may be uneven, depending on the attraction between the polypeptide 110 located on the single charged cell 118 and the charged graphene complex 100, and on the physical location of metal-attached polypeptides over the surface of the cell. A process of producing the final complex 114 is described in FIG. 5.

Figure 5:
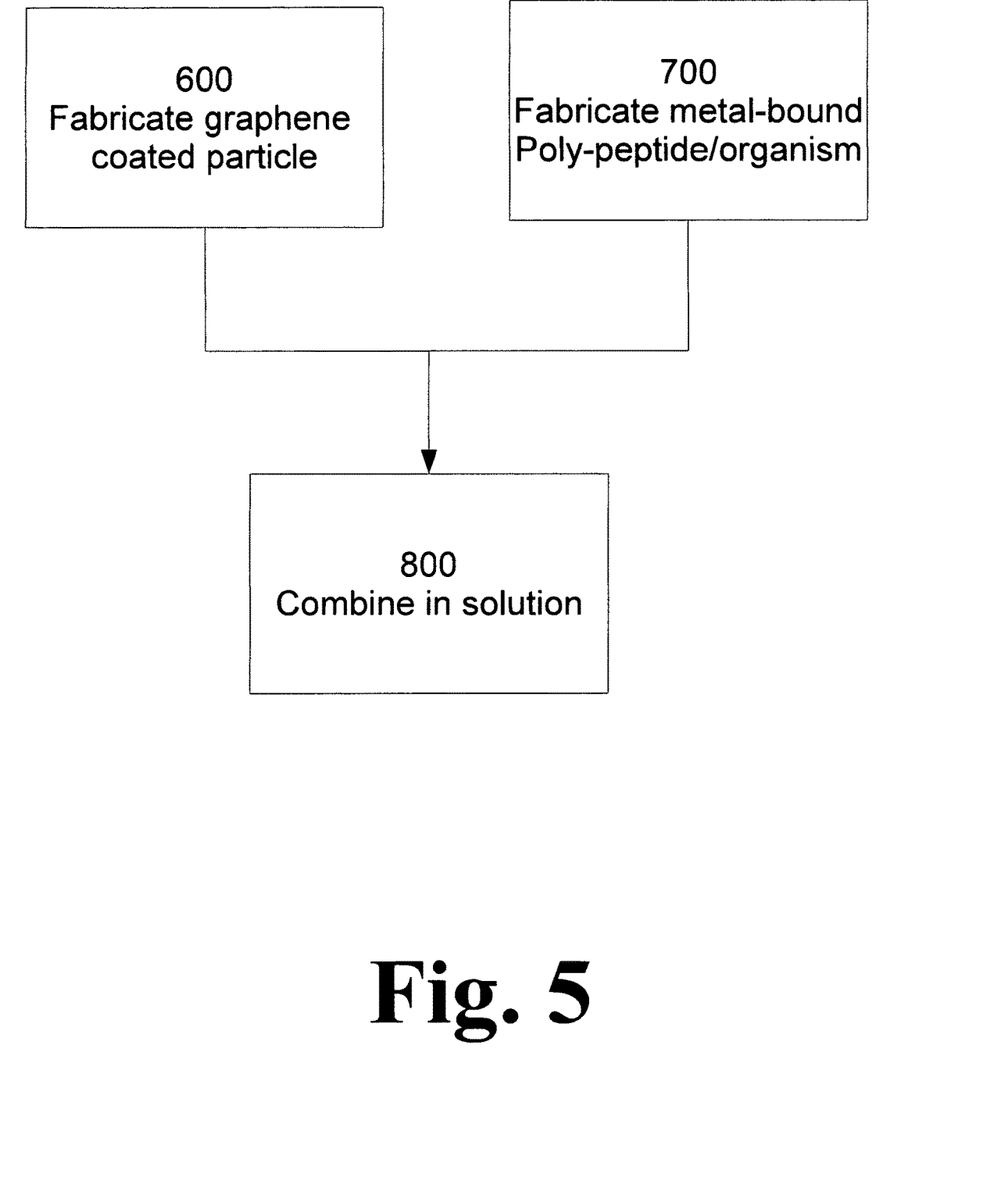
FIG. 5 is an example method of fabricating a complex as shown in FIG. 4.

Shown in FIG. 5 is high-level example method of fabricating complex 114, according to aspects of the inventive concepts. In process 600, a chemically active graphene coated particle 100 is fabricated. This process is elaborated on in FIG. 6, below. At process step 700, a metal-attached polypeptide or single-celled organism 108 is produced. Details of this process are further described in FIG. 7. In process step 800, the complex 114 is created by combining the charged graphene coated particle complex 100 produced in process step 600 with the metal-attached polypeptide 108 or charged single cell organism 118 produced in process 700. The graphene coated particle 100 may act as a delivery mechanism for a polypeptide 110 or single celled organism 116 when combined into a complex 114. Alternatively, in some embodiments, the method for creating complex 114 may be used to precipitate out, or otherwise bind to biological entities (such as mold spores) in the environment.

Figure 6:
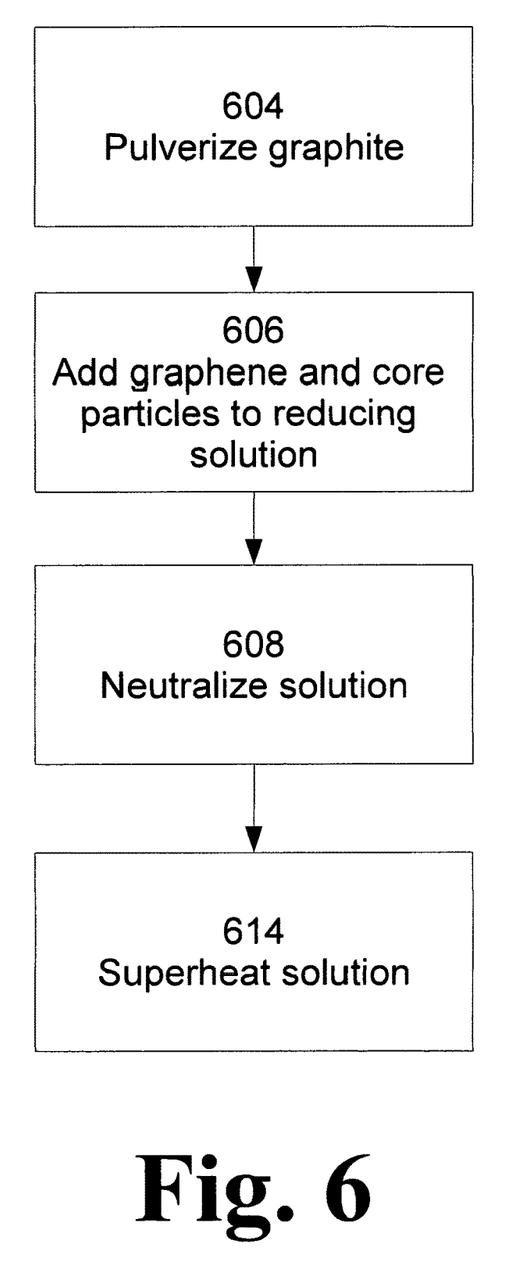
FIG. 6 is an illustration of an example method for generating a chemically active graphene coated particle.

Shown in FIG. 6 is an example method 600 for producing a chemically active (negatively charged, or basic) graphene coated particle complex 100 according to aspects of the inventive concepts. The method 600 may consist of a step 604: pulverizing graphite, a step 606: adding to a reducing solution graphene and core particles 110, where in during the resulting REDOX reaction the resulting oxygen is off-gassed and depleted, a step 608: neutralizing the mixture of 606, and 614: superheating the mixture of 608 to create the chemically active graphene coated particles 100.

More specifically, in some embodiments, the core particle 102 may be any type of inert, dielectric material and may include, for example, silica, coal, or diatomaceous earth. At step 604, in some embodiments, the graphite can be milled to 0.5 to 10 micron sized particles. In some embodiments, at step 606 the pulverized graphite can be immersed with the core particles in a reducing solution of sodium hydroxide diluted to 5 to 10 mol, and combined with ammonia. The immersion time of this step may be about 10 minutes to an hour. In some embodiments, the solution is cooled overnight at room temperature in a water bath, dry-ice or a dry-ice/acetone bath to control the temperature of the reaction. After the immersion mixture is cooled to room temperature, nitrogen gas may be bubbled into the solution used to reduce any resulting oxygen.

In some embodiments, at step 608, the mixture's pH can then be neutralized or adjusted to a pH of 6.0-7.0 by a sodium or potassium base salt or ammonium salt, or the like, thus producing a hydroxide ion that imparts a negative charge to the graphene. The mixture is then superheated in step 614 to produce the charged graphene-core particle complex 100. The heating method may be a microwave or other heat source.

The result of example process 600 is a core particle coated with graphene having negatively charged or basic groups attached: a charged graphene coated particle complex 100. Without being limited by theory, the charged graphene coated particle complex 100 resulting from step 614 may comprise of a core 102 that is coated with a graphene shell 104 that carries for example, a basic hydroxy group 106 that may attract the positively charged metal ion(s) 112 of the charged polypeptide or single-celled organism 108. This graphene coated complex 100 is capable of holding a negative electrical or chemical charge or basic group 106, and has the capacity to attract, bind and potentially become a carrier for a positively charged (or metal bound) polypeptide 108 or single-celled organism 118.

Figure 7:
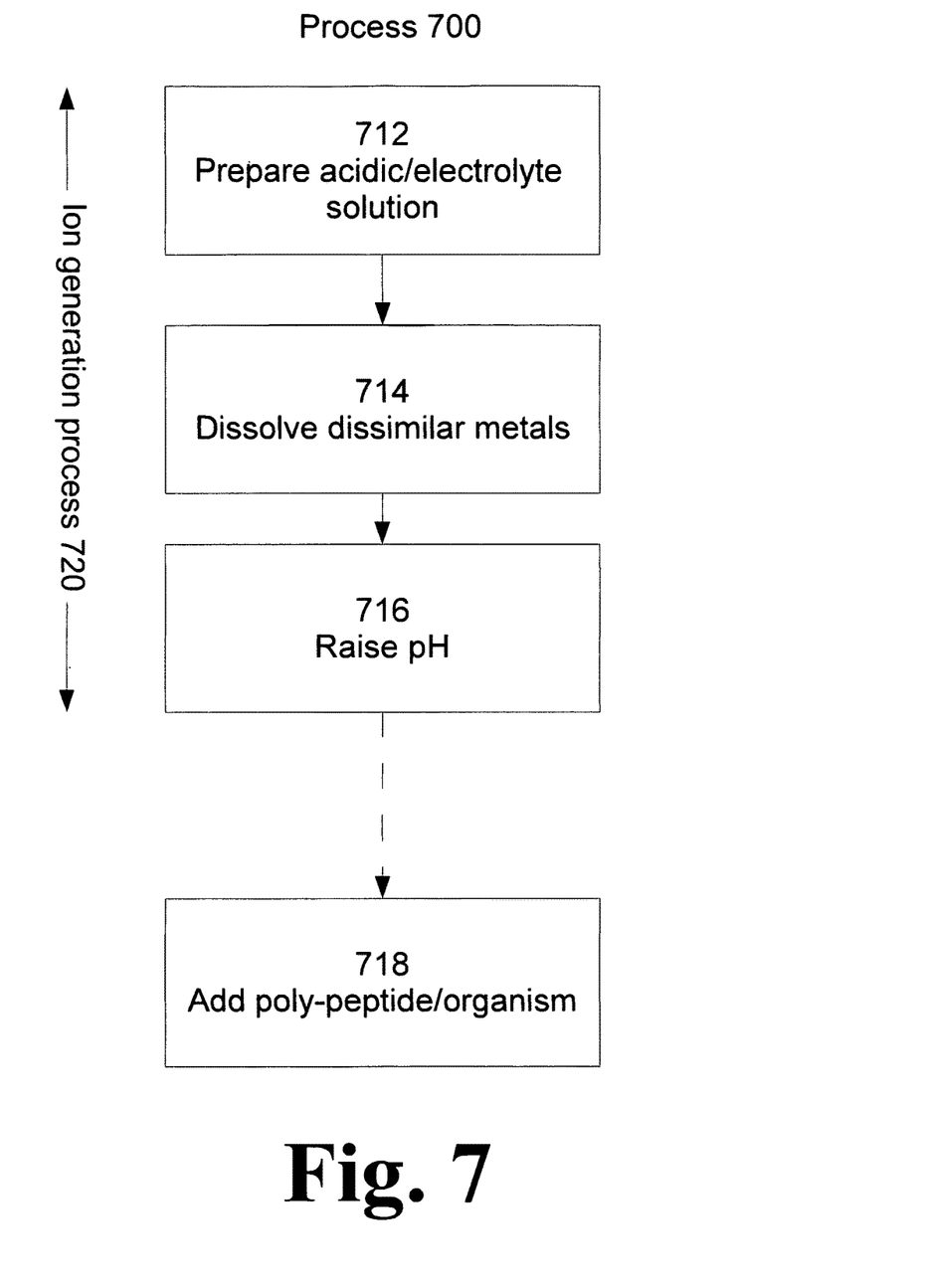
FIG. 7 is an illustration of an example method for generating a metal-bound polypeptide or organism according to embodiments of the invention.

Shown in FIG. 7 is an example method 700 for generating metal-attached polypeptide 108 or single celled organism 118 according to aspects of the inventive concepts. In some embodiments, the process of producing a metal-attached polypeptide 108 or single cell organism 118 is conducted at room temperature, and consists of a ion generation process 720 conducted at 60-100 F (10-37.8 C) degrees temperature, which consists of an electrolyte solution producing step 712, a dissimilar metal immersion step 714, and a solution neutralization step 716. Process 720 is followed by step 718, where a polypeptide 106 or single celled organism 110 is added into the metal ion solution produced in step 716 to generate the metal-attached polypeptide 108 or single-celled organism 118.

More specifically, in some embodiments, in step 712, an electrolyte solution is produced. The dilute electrolyte solution may be made with a ratio of 1:10 up to 1:100 acid to water. The acid may be phosphoric, sulfuric, hydriodic, or hydrochloric acid, or a weaker acid such as citric or acetic acid, or a combination of acids (see Table 1, below). The pH of the electrolyte solution may be under 4.0. At step 714, two metals of dissimilar electrical potential and biological importance, such as transitional metals like Cu and Mn may be dissolved in the electrolyte solution. The metals added during step 714 are in the form of large particles, or are milled, ground, or screened 1 to 10 micron or larger sized particles. After the metals are dissolved in the electrolyte solution, the solution's pH may be raised to about 6-7 instep 716, by adding a sodium or potassium base salt (such as sodium hydroxide), or the like in step 714, which produces a positively charged metal ion solution. The poly peptide 110 or single-celled organism 116 is then imbued with charged metal ion 112 by immersing a solution of the polypeptide in the metal ion solution in step 718. In alternative embodiments, step 718 may be carried out with a suspension of single celled organism 118 having on them polypeptides 110 that are capable of binding a charged metal ion. Without being bound by theory, the resulting complex produced in step 718 can be a charged polypeptide or single celled organism 108, which may comprise of a polypeptide 110 or single celled organism 116 with a with a positively charged ion 112 attached to it at a receptor site.

Returning to FIG. 5, once the graphene coated particles have been prepared according to process 600 of FIG. 6, and the metal-attached polypeptides 108 or single-celled organisms 118 have been prepared, the two can be combined at step 800 to produce complex 114 of metal-attached peptides (or organisms) attached to graphene coated particles.

In alternative embodiments, complex 114 may be produced in an alternative way. Before being added to the ploy-peptide 110 or single-celled organisms 116 at step 718, the electrolyte solution prepared in process 720 may instead be added directly to the graphene particles produced as a result of process 600. This produces a composition consisting on a graphene coated particle with a basic surface coating which is in turn bound to the metal ions of the solution prepared in 720. This new mixture may be sprayed, soaked or otherwise applied to the environment to bind to polypeptides 110 or single celled organisms 116 (such as mold spores) in the environment in-situ, producing complex 114. If the mixing is performed in environmental water, this may result in a purification of the water.

It has been observed that creating the complex 114 in-situ as described above causes mold spores, bacteria, and other microscopic biologicals to aggregate and come out of suspension in air and water, making it substantially easier to clean or disinfect surfaces.

Furthermore, it has been observed that spraying the solution of complex 114 results in a surface coating of the complex 114 on the target of spraying or immersing that is both even and resistant to removal. Thus, creating and applying a complex of 114 wherein the polypeptide 110 has biologic activity (such as a pesticide) may be an effective mechanism of distributing such biologically active polypeptide and effectuating its purpose.

TABLE 1 sample basic and acidic solutions applicable to the processes herein

| Anode-oxidation | pH | pH | pH |
|---|---|---|---|
| ALKALI SOLUTIONS | 1 mM | 10 mN | 100 mM |
| Potassium hydroxide (KOH) | 10.98 | 11.95 | 12.88 |
| Sodium Hydroxide (NaOH) | 10.98 | 11.95 | 12.88 |
| Sodium Metacilicate (Na2SiO3) | 11.00 | 11.91 | 12.63 |
| Ammonium hydroxide (NH4OH) | 10.09 | 10.61 | 11.13 |
| ACID SOLUTIONS | | | |
| Stronger acids | | | |
| Sulfuric acid (H2SO4) | 2.75 | 1.87 | 1.01 |
| Hydrochloric acid (HCL) | 3.01 | 2.04 | 1.08 |
| Phosphoric acid (H3PO4) | 3.06 | 2.26 | 1.63 |
| Weaker acids | | | |
| Citric acid (C6H8O7) | 3.24 | 2.62 | 2.08 |
| Lactic acid (C3H6O3) | 3.91 | 3.39 | 2.88 |
| Acetic acid (C2H4O2) | 3.91 | 3.39 | 2.88 |

I claim:

1. A method for producing a graphene coated particle comprising:
   a. grinding graphite to 0.5 to 10 microns in size,
   b. adding the ground graphite to a basic solution,
   c. adding core particles to the basic solution,
   d. neutralizing the basic solution, and,
   e. superheating the solution.

2. The method of claim 1 wherein the basic solution is a dilute solution of one or more of: potassium hydroxide and sodium hydroxide.

3. The method of claim 1 wherein the basic solution is neutralized to a PH of 6.0 to 7.0.

4. The method of claim 1 further comprising adding a solution of metal ions to the solution.

5. The method of claim 4 wherein the solution of metal ions is a produced from combining the metal with a solution of one or more of: sulfuric acid, phosphoric acid, or hydroiodic acid, hydrochloric acid, acetic acid and citric acid.

6. The method of claim 5 further comprising adding one or more polypeptides to the solution.

7. The method of claim 6 wherein the one or more polypeptide is a biologically active molecule.

* * * * *